US008580490B1

(12) United States Patent
Belisle et al.

(10) Patent No.: US 8,580,490 B1
(45) Date of Patent: Nov. 12, 2013

(54) MARKERS FOR SCREENING ANTI-MYCOBACTERIAL TREATMENT EFFICACY

(75) Inventors: John T. Belisle, Fort Collins, CO (US); Sebabrata Mahapatra, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 51 days.

(21) Appl. No.: 13/153,824

(22) Filed: Jun. 6, 2011

Related U.S. Application Data

(60) Provisional application No. 61/351,343, filed on Jun. 4, 2010.

(51) Int. Cl.
*C12Q 1/00* (2006.01)
*A61K 39/04* (2006.01)
*A61K 39/02* (2006.01)

(52) U.S. Cl.
USPC .............. 435/4; 424/9.1; 424/9.2; 424/234.1; 424/248.1

(58) Field of Classification Search
USPC ................... 424/9.1, 9.2, 234.1, 248.1; 435/4
See application file for complete search history.

(56) References Cited

U.S. PATENT DOCUMENTS 5,023,252 A 6/1991 Hseih

OTHER PUBLICATIONS

Bain, et al., "Contribution of Gut Bacterial Metabolism to Human Metabolic Disease", The Lancet, pp. 1078-1079, May 14, 1988.
Basaraba, "Experimental Tuberculosis: The Role of Comparative Pathology in the Discovery of Improved Tuberculosis Treatment Strategies", Tuberculosis (2008) 88 Suppl. 1, pp. S35-S47.
Bollard, et al., "NMR-Based Metabonomic Approaches for Evaluating Physiological Influences on Biofluid Composition", NMR in Biomedicine, 2005, 18:143-162.
Cone, et al., "Normalization of Urinary Drug Concentrations with Specific Gravity and Creatinine", Journal of Analytical Toxicology, vol. 33, pp. 1-7, Jan./Feb. 2009.
DesJardin, et al., "Measurement of Sputum Mycobacterium Tuberculosis Messenger RNA as a Surrogate for Response to Chemotherapy", Am J Respir Crit Care Med, vol. 160, pp. 203-210, 1999.
Dettmer, et al., "Mass Spectrometry-Based Metabolomics", Mass Spectrometry Reviews, 26, pp. 51-78, 2007.
Dheda, et al., "Lung Remodeling in Pulmonary Tuberculosis", JID 192:1201-1210, 2005.
Donald, et al., "The Early Bactericidal Activity of Anti-Tuberculosis Drugs: A Literature Review",Tuberculosis 88 Suppl. 1, pp. S75-S83. 2008.
Dye, et al., "Evolution of Tuberculosis Control and Prospects for Reducing Tuberculosis Incidence, Prevalence, and Deaths Globally", JAMA, vol. 293, No. 22, pp. 2767-2775, Jun. 8, 2005.
Gowda, et al., "Metabolomics-Based Methods for Early Disease Diagnostics". Expert Review of Molecular Diagnostics, 8.5, pp. 617-633, Sep. 2008.
Harries, et al., "The HIV-Associate Tuberculosis Epidemic—When Will We Act?", Lancet, vol. 375 pp. 1906-1919, May. 29, 2010.
Johnson, et al., "Randomized Trial of Adjunctive Interleukin-2 in Adults with Pulmonary Tuberculosis", Am J Respir Crit Care Med, vol. 168, pp. 185-191, 2003.
Johnson, et al., "Urine PGE-M: A Metabolite of Prostaglandin E2 as a Potential Biomarker of Advanced Colorectal Neoplasia", Clinical Gastroenterology and Hepatology, 4:1358-1365, 2006.
Kaddurah-Daouk, et al., "Metabolomics: A Global Biochemical Approach to Drug Response and Disease", Annu. Rev. Pharmacol. Toxicol., 48:653-683, 2008.
Kim, et al, "Urine Metabolomics Analysis for Kidney Cancer Detection and Biomarker Discovery", Molecular & Cellular Proteomics 8.3, pp. 558-570, 2009.
Li, et al., "Sputum Mycobacterium Tuberculosis mRNA as a Marker of Bacteriologic Clearance in Response to Antituberculosis Therapy", Journal of Clinical Microbiology, vol. 48, No. 1, pp. 46-51, Jan. 2010.
Locht, et al., "How a Different Look at Latency Can Help to Develop Novel Diagnostics and Vaccines Against Tuberculosis", Expert Opin. Biol. Ther., 7(11):1665-1677, 2007.
Lonnroth, et al., "Tuberculosis Control and Elimination 2010-50: Cure, Care, and Social Development", Lancet vol. 375, 1814-1829, May 22, 2010.
Lysov, at al., "Connective Tissue Metabolic Parameters in Differential Diagnosis of Infiltrative Pulmonary Tuberculosis and Pneumonia in Patients with Signs of Connective Tissue Dysplasia", Probl Tuberk Bolezn Legk., (11)11-3, 2003, Abstract.
Ma, et al., "Global Tuberculosis Drug Development Pipeline: The Need and the Reality", Lancet, vol. 375, 2100-2109, Jun. 12, 2010.
Mistry, et al., "Gene-Expression Patterns in Whole Blood Indentity Subjects at Risk for Recurrent Tuberculosis", JID 195, pp. 357-365, 2007.
Mitchison, D.A., "Assessment of New Sterilizing Drugs for Treating Pulmonary Tuberculosis by Culture at 2 Months", The American Review of Respiratory Disease, vol. 147, pp. 1062-1063, 1993.

(Continued)

*Primary Examiner* — Rodney P. Swartz
(74) *Attorney, Agent, or Firm* — Michael M. McGaw; Smith & Hopen, P.A.

(57) ABSTRACT

A method for metabolomically evaluating a subject's response to an anti-mycobacterial agent. The method includes the steps of generating multiple small molecule profiles using samples collected from the subject at or immediately prior to the start of treatment and at a times subsequent to the start of treatment with the anti-mycobacterial agent, identifying predetermined biomarkers in the small molecule profiles of the subject and comparing to a known standard established for the agent as an indication of whether the human is benefiting from treatment with the agent. Also provided are methods of monitoring treatment compliance, methods for establishing biomarkers indicative of treatment efficacy and validated biomarkers shown to be effective in assessing efficacy of anti-tuberculosis drugs.

15 Claims, 8 Drawing Sheets

(56) References Cited

OTHER PUBLICATIONS

Nam, et al., "Combining Tissue Transcriptomics and Urine Metabolomics for Breast Cancer Biomarker identification", Bioinformatics, vol. 25, No. 23, pp. 3151-3157, 2009.

Nicholls, et al., "NMR Spectroscopic-Based Metabonomic Studies of Urinary Metabolite Variation in Acclimatizing Germ-Free Rats", Chem. Res Toxicol., vol. 16, No. 11, pp. 1395-1404, 2003.

Nyendak, et al. "New Diagnostic Methods for Tuberculosis", Current Opinion in Infectious Diseases, 22:174-182, 2009.

Pai, et al., "T-Cell Assays for the Diagnosis of Latent Tuberculosis Infection: Moving the Research Agenda Forward", Lancet Infect. Dis. 7:428-438, Jun. 2007.

Parida, et al., "The Quest for Biornarkers in Tuberculosis", Drug Discovery Today, vol. 15, No. 3/4, pp. 148-157, Feb. 2010.

Pawelec, "Urinary Excretion of Hydroxproline in Tuberculosis", Gruzlica, vol. 40:913-918, 1972, Poland.

Perrin, et al., "Biomarfers of Treatment Response Clinical Trials of Novel Antituberculosis Agents", Lancet Infect Dis, vol. 7:481-490, 2007.

Smilde, et al., "Dynamic Metabolomic Data Analysis: A Tutorial Review", Metabolomics 6:3-17, 2010.

Smith, et al., "METLIN A Metabolite Mass Spectral Database", Therapeutic Drug Monitoring, vol. 27, No. 6, 747-751, Dec. 2005.

Syhre, et al., "The Scent of Mycobacterium Tuberculosis", Tuberculosis 88:317-323, 2008.

Syhre, et al., "The Scent of Mycobacterium Tuberculosis—Part II Breath", Tuberculosis 89:263-266, 2009.

Vinayavekhin, et al., "Exploring Disease Through Metabolomics", ACS Chemical Biology, vol. 5, No. 1, 91-103, 2010.

Vinnik, et al., "Oxyproine Metabolism in Patients with Pulmonary Tuberculosis", Problemy Tuberkuleza, vol. 50(4), pp. 67-72, 1972.

Wallis, et al., "Biomarkers and Diagnostics for Tuberculosis: Progress, Needs, and Translation into Practice", Lancet, vol. 375: 1920-1937, May 29, 2010.

Wallis "Surrogate Markers to Assess New Therapies for Drug-Resistant Tuberculosis", Expert Rev. Anti Infect. Ther. 5(2), pp. 163-168, 2007.

Walzl, et al., "Biomarkers for TB Treatment Response: Challenges and Future Strategies", Journal of Infection, 57:103-09, 2008.

Wishart, et al., "HMDB: A Knowledgebase for the Human Metabolom", Nucleic Acids Research, vol. 37, pp. D603-D610, 2009.

Zhang, et al., "Quantification of the Oxidative Damage Biomarker 2,3-dinor-8-isoprostaglandin-F2alpha in Human Urine Using Liquid Chromatography-Tandem Mass Spectrometry", Analytical Biochemistry, 399:302-304, 2010.

Extract molecular features* and their abundance from each data file
(Molecular feature Extractor of the Mass Hunter Workstation software)

Normalize and compare the relative abundance of molecular features
from untreated and treatment groups
(Agilient Mass Profiler Pro Software)

List of molecular features that vary significantly in abundance
following treatment with exact masses and predicted molecular
formulas

*Molecular features = metabolites (defined by a specific mass present at a specific retention time).

*Figure 3*

MARKERS FOR SCREENING ANTI-MYCOBACTERIAL TREATMENT EFFICACY

CROSS REFERENCE TO RELATED APPLICATIONS

This application claims priority to currently pending U.S. Provisional Patent Application 61/351,343, entitled, "Identification of Surrogate Marker to Assess the Efficacy of Drug Treatment for Tuberculosis", filed Jun. 4, 2010, the contents of which are herein incorporated by reference.

STATEMENT OF GOVERNMENT INTEREST

This invention was made with government support under Grant No. NO1 AI070022 awarded by the National Institutes of Health. The government has certain rights in the invention.

FIELD OF INVENTION

This invention relates to methods for treating pathogenic infections in mammals. More specifically, this invention relates to the identification of surrogate markers to assess the efficacy of treatment for tuberculosis and infections resulting from other *Mycobacterium* species.

BACKGROUND OF THE INVENTION

One of the major goals of the World Health Organization is to reduce the prevalence of TB to half by 2015, and eliminate it as a public health threat by 2050 [Dye C, et al., *JAMA*. 2005; 293(22):2767-75; Lonnroth K, et al., *Lancet*. 2010; 375(9728):1814-29]. An essential element required to achieve this goal is the development and implementation of new drugs to treat multiple drug resistant (MDR) and extensively drug resistant (XDR) tuberculosis as well as new drugs to for preventative treatment of latent *M. tuberculosis* infections. At present four existing drugs and six recently developed drugs are in clinical trials for their effectiveness in treating tuberculosis [Ma Z, et al., *Lancet*. 2010; 375(9731): 2100-9] and the Global Alliance for TB Drug Development lists at least 15 additional products and drug groups in preclinical development. Although the number of compounds in the drug development pipeline is encouraging, there remain several scientific and operational impediments to their rapid introduction into treatment regimens [Ma Z, et al., *Lancet*. 2010; 375(9731):2100-9]. As potentially new drugs progress through the developmental pipeline, the continued emergence of MDR and XDR tuberculosis and the co-prevalence of tuberculosis with HIV add additional pressures to strained tuberculosis control programs [Harries A D, et al., *Lancet*. 2010; 375(9729):1906-19].

One scientific challenge noted in several reviews as an accelerator for TB drug development [Ma Z, et al., *Lancet*. 2010; 375(9731):2100-9; Parida S K, et al., *Drug Discov Today*. 2010; 15(3-4):148-57; Wallis R S, et al., *Lancet*. 2010; 375(9729):1920-37] and also emphasized in the FDA Office of Critical Path Programs' RFA SF424 RR is the development of "biomarkers" for cure and/or prediction of long-term outcome. The traditional endpoint of licensing trials for anti-TB drugs and regimens is cure without relapse at one to two years after the end of treatment. Thus, trials to evaluate new TB drugs commonly require two to four years to complete. Initial phases of clinical trials use two-month culture conversion and extended early bactericidal activity (EBA) assays to demonstrate sufficient efficacy to move products forward [Donald P R, et al., *Tuberculosis (Edinb)*. 2008; 88 Suppl 1:S75-83; Ma Z, et al., *Lancet*. 2010; 375(9731):2100-9]. However, the requirement for long-term follow-up in Phase III trials and the use of resource and labor intensive methods such as quantitative culture/colony forming unit (CFU) assays increases the time and cost of evaluating drugs for TB treatment. The identification of biomarkers, or biosignatures, that serve as surrogate endpoints for cure would greatly enhance clinical trials by decreasing the time and cost required to determine treatment efficacy.

Biomarkers of response to TB treatment may reflect changes in the host as well as the pathogen and there are a large number of biological processes or molecules that can serve as biomarkers [Parida S K, et al., *Drug Discov Today*. 2010; 15(3-4):148-57]. Currently, applied diagnostic approaches that monitor the adaptive immune response of the host (T cell and antibody responses) are likely poor surrogates for the prediction of cure during the treatment of tuberculosis since the immune response is typically long-lived and can be primed by antigens released from dying or dead bacilli [Wallis R S, et al., *Lancet*. 2010; 375(9729):1920-37; Locht C, et al., *Expert Opin Biol Ther*. 2007; 7(11):1665-77; Nyendak M R, et al., *Curr Opin Infect Dis*. 2009; 22(2):174-82; Pai M, et al., *Lancet Infect Dis*. 2007; 7(6):428-38]. Likewise, the monitoring of pathogen macromolecules (antigen detection) to assess drug efficacy could vary depending on pathogen load and be prolonged as the host tries to clear the dead bacilli.

The monitoring of the transcriptome has demonstrated some success. In a study performed with sputum samples from EBA trials comparing INH, rifampin, and rifalazil and patients on standard short course chemotherapy, the levels in sputum of the *M. tuberculosis* fbpB (fibronectin-binding protein/85B) and hspX (alpha-crystalline homologue) declined rapidly in parallel with sputum CFU counts during treatment [Desjardin L E, et al., *Am J Respir Crit Care Med*. 1999; 160(1):203-10]. However, cultures remained positive after mRNAs became undetectable. A second study found that sputum icl (encoding the isocitrate lyase enzyme from the *M. tuberculosis* glyoxylate cycle pathway) mRNA levels correlated highly with sputum CFU during the first seven days of treatment, remained detectable after one and two months of standard TB therapy and correlated with culture positivity on solid media [Li L, et al., *J Clin Microbiol*. 2010; 48(1):46-51. PMCID: 2812283]. The monitoring of host gene expression profiles also revealed a diagnostic signature for patients with relapsing disease in comparison to healthy controls and active tuberculosis patients [Mistry R, et al., *J Infect Dis*. 2007; 195(3):357-65]. The down-sides to transcriptome monitoring are extensive sample processing and the inability to normalize data from sputum samples.

Currently, the only accepted biomarker for sterilizing activity of tuberculosis drug regimens is conversion of sputum to culture negative on solid media after two months of drug treatment [Ma Z, et al., *Lancet*. 2010; 375(9731):2100-9]. Thus, there is an urgent need to find alternative biomarkers that not only predict a person's response to treatment regimen but also serve as a surrogate endpoint for cure. The present invention provides such markers, fulfilling an important need in the art to allow for the assessment of the efficacy of drug treatment for tuberculosis.

SUMMARY OF THE INVENTION

The only currently accepted biomarker for sterilizing activity of tuberculosis drug regimens is conversion of sputum to culture negative on solid media after two months of drug treatment [Ma Z, et al., *Lancet*. 2010; 375(9730:2100-

9]. Thus, there is an urgent need to find alternative biomarkers that not only predict a person's response to treatment regimen but also serve as a surrogate endpoint for cure. Metabolomics is a novel approach to biomarker discovery for tuberculosis and in particular as a predictor of cure or treatment failure. The pathology associated with tuberculosis is well-described [Basaraba R J, *Tuberculosis* (*Edinb*). 2008; 88 Suppl 1:S35-47; Dheda K, et al., *J Infect Dis.* 2005; 192(7):1201-9] and many of the key effectors produced by the host and the pathogen that lead to active disease are also well-described. These effectors, however, do not provide a snap-shot of the phenotype of tuberculosis at a molecular level. To achieve this requires a measurement of the biochemistry of the system.

The use of metabolomics provides this biochemical snap-shot. As the insult to the system is removed with the use of anti-tuberculosis drugs the biochemistry of the system will also re-adjust to that of the non-diseased state. This flux in the biochemistry of a tuberculosis patient can be measured with state-of-the-art techniques such as high resolution mass spectrometry [Dettmer K, et al., *Mass Spectrom Rev.* 2007; 26(1): 51-78. PMCID: 1904337] and the complexity of the data deconvoluted with algorthims designed to compare across large data sets and extract the relevant information leading to unique biomarkers or biosignatures [Smilde A K, et al., *Metabolomics.* 2010; 6(1):3-17. PMCID: 2834778; Vinayavekhin N, et al., *ACS Chem Biol.* 2010; 5(1):91-103]. The application of metabolomics to identify and validate biomarkers of cure is also more robust because it does not rely on the identification of a single marker or product, but surveys a plurality of small molecules to identify unique signatures that differentiate (1) individuals with active disease from (2) those individuals that are effectively resolving the disease with anti-tuberculosis treatment and (3) those individuals that are not properly responding to treatment (i.e. treatment failures). Additionally, the broad snap-shot of a biological system provided by metabolomics allows evaluation and comparison of treatment on different forms of tuberculosis and treatment response in the presence of co-infection with HIV and anti-retroviral therapy.

In a first aspect the present invention provides a method of evaluating treatment efficacy in a subject undergoing anti-microbial therapy for a *Mycobacterium* species. The method includes the steps of administering a regimen of anti-mycobacterial treatment to the subject, providing at least two samples from the subject undergoing treatment, measuring the change in a plurality of metabolomic markers between at least two samples and correlating the measured change in markers with a predetermined treatment efficacy. When performing the method of the first aspect, the first sample is taken at or before the beginning of the treatment regimen and the second sample is taken at a later time following the initiation of treatment. The method can further include the step of adjusting the treatment regimen responsive to the correlated treatment efficacy.

Advantageous sources of samples include urine, sputum, plasma, and serum. With respect to the second sample, it can be taken at times such as about one week following the initiation of treatment, two weeks, four weeks, six weeks following the initiation of treatment, about two months following the initiation of treatment, three months, four months, five months, six months, seven months, eight months, nine months, twelve months, eighteen months, or about twenty-four months following the initiation of treatment. Multiple samples can also be taken, such as at the aforementioned time-points.

In an advantageous embodiment at least one of the plurality of markers can be Hydroxyproline, N-Acetyl-L-aspartic acid, Dimethyl-L-arginine, N-Acetylasparagine, 1-Methylhistidine, L-Phenylalanine, 2,2,5,5-Tetramethyl-3-pyrrolidinecarboxamide, Pyroglutamic acid, Acetylcysteine, Trigonelline, S-Adenosylhomocysteine, L-Tyrosine, alpha-Aminoadipic acid, Quinolinic acid, Hypoxanthine, or Pyrroline hydroxycarboxylic acid. Similarly, at least one of the plurality of markers can have a mass selected from the group consisting of about 109.002, about 147.053, about 166.048, about 183.162, about 206.025, about 267.256, about 277.241, about 279.615, about 280.044, about 281.273, about 295.252, about 357.973, about 388.104, about 406.068, about 410.750, about 428.080, about 444.112, about 463.306, about 499.003, about 504.277, about 534.248, about 545.299, about 557.290, about 609.303, about 654.372, about 696.519, about 742.426, about 799.573, about 805.239, about 817.583, about 850.392, about 859.657, and about 866.366.

In further advantageous embodiments according to the first aspect of the invention the subject can be undergoing treatment with a drug such as isoniazid, rifampin, rifalazil ethambutol, pyrazinamide, amikacin, moxifloxacin, ciprofloxacin, ofloxacin, kanamycinm, levofloxacin, ethambutol, aminosalicyclic acid, rifapentine, cycloserine, ethionamide, capreomycin, gatifloxacin, viomycin, envyomicin or combinations thereof. Most advantageously the anti-mycobacterial therapy is INH, rifampin, or rifalazil. The infection being treated can be due to a *Mycobacterium* species such as *Mycobacterium tuberculosis*, *Mycobacterium bovis*, *Mycobacterium bovis BCG*, *Mycobacterium africanum*, *Mycobacterium canetti*, *Mycobacterium caprae*, *Mycobacterium pinnipedii*, *Mycobacterium leprae*, *Mycobacterium ulcerans*, *Mycobacterium abscessus*, and *Mycobacterium paratuberculosis*.

In a second aspect the present invention provides a method for metabolomically evaluating a subject's response to an anti-mycobacterial agent. The method includes the steps of generating a first small molecule profile from the subject using samples collected from the subject at or immediately prior to the start of treatment with the anti-mycobacterial agent, generating a second small molecule profile from the subject using samples collected from the subject at a time subsequent to the start of treatment with the anti-mycobacterial agent, and comparing the change in the small molecule profile of the subject to a known standard established for the agent as an indication of whether the human is benefiting from treatment with the agent. The known standard can be obtained from a defined population of humans treated with the agent. This allows for a prediction of a subject's response to the anti-mycobacterial agent. The method of the second aspect can include the step of identifying a plurality of metabolomic markers within the first and second small molecule profile and comparing the change in the metabolomic markers of the subject to a known standard established for the agent. The method according to claim 11, further comprising the step of administering a regimen of anti-mycobacterial treatment to the subject.

Small molecule profiles are obtained using one or more of the following: HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), gas chromatography (GC) and Light Scattering analysis (LS).

In an advantageous embodiment at least one of the plurality of markers can be Hydroxyproline, N-Acetyl-L-aspartic acid, Dimethyl-L-arginine, N-Acetylasparagine, 1-Methylhistidine, L-Phenylalanine, 2,2,5,5-Tetramethyl-3-pyrrolidinecarboxamide, Pyroglutamic acid, Acetylcysteine, Trigonelline, S-Adenosylhomocysteine, L-Tyrosine, alpha- Aminoadipic acid, Quinolinic acid, Hypoxanthine, or Pyrroline hydroxycarboxylic acid. Similarly, at least one of the plurality of markers can have a mass selected from the group consisting of about 109.002, about 147.053, about 166.048, about 183.162, about 206.025, about 267.256, about 277.241, about 279.615, about 280.044, about 281.273, about 295.252, about 357.973, about 388.104, about 406.068, about 410.750, about 428.080, about 444.112, about 463.306, about 499.003, about 504.277, about 534.248, about 545.299, about 557.290, about 609.303, about 654.372, about 696.519, about 742.426, about 799.573, about 805.239, about 817.583, about 850.392, about 859.657, and about 866.366.

In further advantageous embodiments according to the second aspect of the invention the subject can be undergoing treatment with a drug such as isoniazid, rifampin, rifalazil ethambutol, pyrazinamide, amikacin, moxifloxacin, ciprofloxacin, ofloxacin, kanamycinm, levofloxacin, ethambutol, aminosalicyclic acid, rifapentine, cycloserine, ethionamide, capreomycin, gatifloxacin, viomycin, envyomicin or combinations thereof. Most advantageously the anti-mycobacterial therapy is INH, rifampin, or rifalazil. Alternatively, the therapeutic agent can be an agent administered during clinical trials.

The infection being treated can be due to a *Mycobacterium* species such as *Mycobacterium tuberculosis, Mycobacterium bovis, Mycobacterium bovis BCG, Mycobacterium africanum, Mycobacterium canetti, Mycobacterium caprae, Mycobacterium pinnipedii, Mycobacterium leprae, Mycobacterium ulcerans, Mycobacterium abscessus*, and *Mycobacterium paratuberculosis*.

Advantageous sources of samples include urine, sputum, plasma, and serum. With respect to the second sample, it can be taken at times such as about one week following the initiation of treatment, two weeks, four weeks, six weeks following the initiation of treatment, about two months following the initiation of treatment, three months, four months, five months, six months, seven months, eight months, nine months, twelve months, eighteen months, or about twenty-four months following the initiation of treatment. Multiple samples can also be taken, such as at the aforementioned time-points.

In a third aspect the present invention provides a method for screening for biomarkers predictive of the efficacy of one or more anti-Mycobacterium species treatment. The method includes the steps of collecting a first sample set from a treatment population prior to or at the start of a treatment regimen, administering an anti-mycobacterial treatment regimen to the treatment population, collecting one or more additional sample sets from the treatment population at a subsequent time after the initiation of the treatment regimen, generating small molecule profiles from each of the collected samples, comparing the change in the small molecule profiles of the treatment population from the first sample set to the subsequent sample sets, selecting metabolomic markers from the compared small molecule profiles, and correlating the selected metabolomic marker with the treatment response of subjects within the treatment population. The markers can be selected based upon an increase or decrease in the abundance of the marker between the first small molecule profile and the subsequent small molecule profiles.

In a fourth aspect the present invention provides a method for monitoring the compliance of a subject with an anti-mycobacterial treatment regimen. The method includes the steps of collecting a first sample from the subject prior to or at the start of a treatment regimen, collecting one or more additional samples from the treatment population at a subsequent time after the initiation of the treatment regimen, screening the samples for a change in one or more metabolomic biomarkers associated with treatment compliance. The absence of a change in the one or more biomarkers is indicative of non-compliance with the treatment regimen.

BRIEF DESCRIPTION OF THE DRAWINGS

For a fuller understanding of the invention, reference should be made to the following detailed description, taken in connection with the accompanying drawings, in which:

FIG. 3 is a diagram illustrating the data analyses and comparisons to extract relevant molecular features across large data sets.

DETAILED DESCRIPTION OF THE PREFERRED EMBODIMENT

Figure 1:
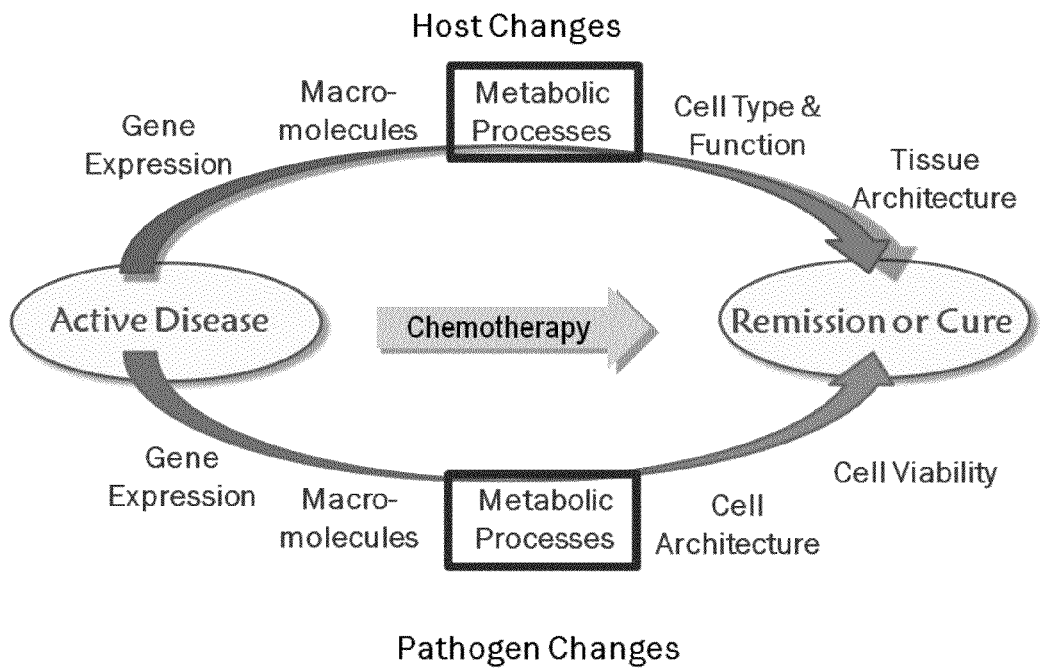
FIG. 1 is a diagram illustrating the target selection for biomarkers of drug treatment.

Clinical trials to evaluate new drugs and regimens for treatment of tuberculosis (TB) are lengthy endeavors due to the slow rate of disease clearance and the slow growth rate of the infecting bacterium, *Mycobacterium tuberculosis*. Thus, studies were performed that identified biochemical markers of either host or bacterial origin from urine samples, where these biomarkers that can serve as surrogate markers of effective anti-tuberculosis therapy. Urine specimens from TB patients collected before and after drug treatment were subjected to liquid chromatography-mass spectrometry and the relative abundance of metabolites present in the pre- and post-chemotherapy samples were compared. This approach identified fifty-eight molecular features (metabolites) that rapidly change in abundance following the onset of treatment. A number of the differentiating features were initially identified and sixteen were more fully characterized. Thus, a large set of novel biomarkers are provided that can be used to predict treatment outcome and potentially primary diagnosis. Additional biomarkers can be identified employing the techniques taught herein.

The successful treatment of TB requires long-term multidrug chemotherapy resulting in poor patient compliance particularly in high burden countries with poor infrastructure. Shortening of the treatment length can significantly improve treatment adherence as well as the emergence and spread of drug resistance TB. New drugs and potentially treatment-shortening regimens are being evaluated by clinical trials. The clinical trials for TB treatment are based on standard 6-9 months of therapy followed by another 1-2 years to measure relapse rates as an indicator of sterilizing efficacy or clinical endpoint [Perrin, F. M. et al., *Lancet Infect. Dis.* 7, 481-490 (2007); Walzl, G. et al., *J. Infect.* 57, 103-109 (2008)]. Currently, the only accepted biomarker for sterilizing activity is conversion to negative sputum culture at month two of treatment which has several limitations and is not suitable for shorter treatment regimens [Perrin, F. M. et al., *Lancet Infect. Dis.* 7, 481-490 (2007); Mitchison, D. A., *Am. Rev. Respir. Dis.* 147, 1062-1063 (1993); Wallis, R. S. Surrogate markers to assess new therapies for drug-resistant tuberculosis. *Expert. Rev. Anti. Infect. Ther.* 5, 163-168 (2007)]. Therefore, there is a need to find alternative biomarkers that will predict a person's response to treatment after a short period of time and serve as surrogate endpoint markers. Such biomarkers can also be used as a tool in individual chemotherapy management for better treatment outcome.

As discussed above, the monitoring of the transcriptome has demonstrated some success. One study found that sputum icl mRNA levels correlated highly with sputum CFU during the first seven days of treatment, remained detectable after one and two months of standard TB therapy and correlated with culture positivity on solid media [Li L, et al., *J Clin Microbiol.* 2010; 48(1):46-51. PMCID: 2812283]. The monitoring of host gene expression profiles also revealed a diagnostic signature for patients with relapsing disease in comparison to healthy controls and active tuberculosis patients [Mistry R, et al., *J Infect Dis.* 2007; 195(3):357-65]. The down-sides to transcriptome monitoring are extensive sample processing and the inability to normalize data from sputum samples. An alternative to transcriptome analyses is to measure downstream products that provide a phenotypic profile.

Given that in any disease state, altered biochemical processes and networks underlie the gross pathology of a disease, a shift in the metabolic profiles serve as phenotypic signatures of disease. Moreover, alterations in the metabolic profile of a specific biological system are the end product of multiple interactions resulting from altered gene expression and protein activities [Kaddurah-Daouk R, et al., *Annu Rev Pharmacol Toxicol.* 2008; 48:653-83]. These changes are reflected in measurable fluxes in the metabolites present in clinical samples such as urine and serum during the course of the disease and during treatment [Kaddurah-Daouk R, et al., *Annu Rev Pharmacol Toxicol.* 2008; 48:653-83; Gowda G A, et al., *Expert Rev Mol Diagn.* 2008; 8(5):617-33].

Advances in mass spectrometry (MS) instrumentation and software to analyze complex MS data sets have allowed for the emergence of the field of metabolomics and the ability to follow metabolic flux [Dettmer K, et al., *Mass Spectrom Rev.* 2007; 26(1):51-78. PMCID: 1904337; Smilde A K, et al., *Metabolomics.* 2010; 6(1):3-17. PMCID: 2834778]. Moreover, analysis of metabolomic profiles in various disease conditions is now finding its niche in the development of diagnostics [Vinayavekhin N, et al., *ACS Chem Biol.* 2010; 5(1): 91-103]. Metabolomic signatures have been defined for numerous diseases ranging from depression to cardiovascular disease to cancer and has been applied to a limited number of infectious diseases [Vinayavekhin N, et al., *ACS Chem Biol.* 2010; 5(1):91-103].

Metabolomics has also proven successful for providing signatures of drug therapy. The significant and well-described changes that occur in the cellular composition and architecture of *M. tuberculosis* infected tissue along with the introduction of the pathogen's biochemistry into the host system would suggest that metabolomic signatures of tuberculosis and treatment should be readily identifiable. Metabolomics, however, has not been widely explored with respect to biomarker discovery for tuberculosis. Metabolomics can provide signatures to distinguish states of *M. tuberculosis* infection and to predict potential non-responders to drug treatment [Parida S K, et al., *Drug Discov Today.* 2010; 15(3-4):148-57]. Others have analyzed volatile compounds of in vitro grown *M. tuberculosis*, as well as the breath of pulmonary tuberculosis patients, and identified several metabolites that are at significantly higher levels in tuberculosis patients as compared to healthy controls [Syhre M, et al., *Tuberculosis (Edinb).* 2009; 89(4):263-6; Syhre M, et al., *Tuberculosis (Edinb).* 2008; 88(4):317-23]. As presented in the present invention, metabolic profiling offers a great but untapped potential for tuberculosis biomarker discovery.

Metabolic profiling provides biomarker, or biosignatures, that can be used to differentiate between treatment failure or and treatment success, they can provide useful information to gauge the progress of treatment two to four weeks into the treatment phase and can provide information to differentiate between durable cure and relapse. Disease states are associated with changes in the biochemistry of a system resulting in abnormal metabolite profiles. Metabolites rapidly change in abundance with alterations of a biological system. Metabolites can be used to monitor host or pathogen changes, thus leveraging these changes to yield critical information about the status of the disease. An overview of these relationships is presented in FIG. 1. Additionally, metabolites typically require minimal manipulation prior to analyses. Therefore, metabolic flux provides a biosignature that delivers critical information without the necessity for extensive manipulation of samples. Despite these benefits, metabolites are relatively unexplored as biomarkers for treatment of bacterial diseases.

Figure 2:
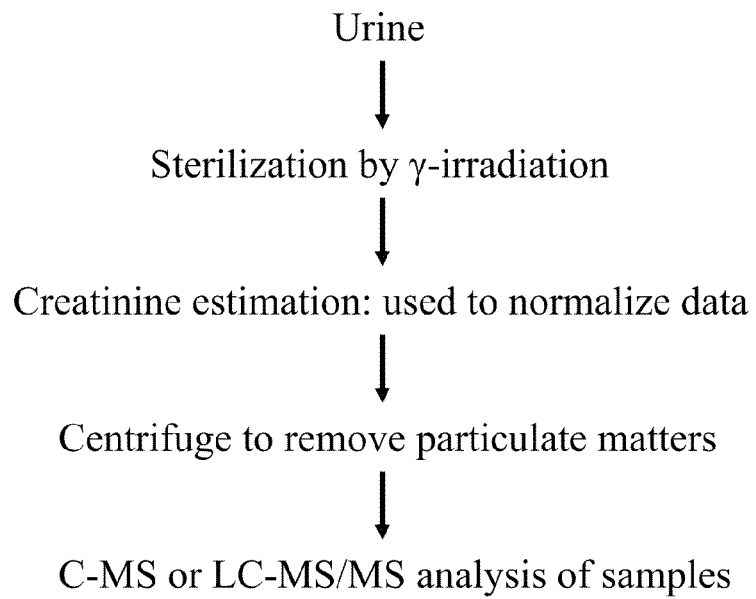
FIG. 2 is a diagram illustrating the steps in the analysis of urine metabolites.

Within the context of tuberculosis and the sampling of other *Mycobacterium* species, there are numerous options for selecting the appropriate biological specimens, including sputum, blood/serum and urine. Sputum samples are currently used for diagnosis and consistent with the fact that most disease is pulmonary. Also, it is easy to equate biomarker abundance to CFUs. Some of the difficulties with sputum samples include that processing may be more difficult and that it is a poor sample source in the instance of non-pulmonary disease. Blood, or serum, provides an alternative to sputum samples. Some benefits of blood include that it does not require chemical processing and standard platforms are available. It also allows an investigation of multiple disease states. Blood samples suffer as a specimen because the collection of blood samples is invasive and the resultant samples are protein rich and complex. Lastly, urine can be used as a biological specimen source. Urine is attractive as a source because it is easy to obtain, standard platforms are available and processing is relatively simple. Shortcomings of using urine as the sample source include that urine is complex and it may only be useful in certain disease states. FIG. 2 illustrates the analysis of urine metabolites. The vast majority of metabolites are found at 800 Daltons and below. Therefore the analysis platform was chosen to focus on metabolites of this class.

A general process of structure identification was employed. First, a query was performed of the exact mass-derived chemical formulas against the human metabolome database or other small molecule structure databases (METLIN). Potential structures were identified based on database hits. MS/MS fragmentation experiments were then performed to limit the pool of potential structures. Structures were confirmed with a commercial reference molecule (LC-MS) by exact mass and retention time.

Human urine contains a large number of metabolites. The urinary pool of metabolites includes a sizable fraction of the human metabolome and metabolites of microbial origin, primarily from normal flora in the GI tract and from pathogenic organisms present in the body during the course of an infection [Bain, M D et al. Lancet 1, 1078-1079 (1988); Nicholls, A W et al., Chem. Res. Toxicol. 16, 1395-1404 (2003)]. Disease states ultimately result from changes in the biochemistry of a system, and metabolomics is the most direct measure of the biochemical profile associated with a disease. Therefore, the urinary metabolome of TB patients can be expected to shift in response to the disease as well as contain metabolites produced by the bacilli. This altered metabolic profile is expected to change gradually towards a normal state (non-disease) in response to successful treatment. Analysis of the metabolome form TB patients before and at different time points of treatment will allow us to identify metabolites, either from human or *M. tuberculosis* that can be used as biomarkers to predict treatment outcome. Based on this hypothesis, we analyzed and compared the urinary metabolome of samples collected from TB patients at the time of initial diagnosis and at different time points during drug treatment.

DEFINITIONS

As used herein, "treating" means treating or ameliorating, and treating or ameliorating means the reduction or complete removal of one or more symptoms of a disease or medical condition, such as tuberculosis. Such treatment or amelioration can include the delay or elimination of the onset of one or more symptoms when administered to a person at risk for the disease or medical condition. Tests for the success of treatment or amelioration are well known in the art.

A subject treated using an agent disclosed herein or identified using methods disclosed herein can be of any age, including a child, juvenile or an adult.

The term "about" or "approximately" as used herein means within 20%, preferably within 10%, and more preferably within 5% of a given value or range.

The term "administration" and variants thereof (e.g., "administering" a compound) in reference to a compound of the invention means introducing the compound into the system of the subject in need of treatment. When a compound of the invention is provided in combination with one or more other active agents (e.g., a cytotoxic agent, etc.), "administration" and its variants are each understood to include concurrent and sequential introduction of the compound and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

A "subject in need of treatment" is a mammal with a Mycobacterium species that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" whereever used herein includes the meaning of "and", "or" and "all or any other combination of the elements connected by said term".

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The invention pertains, at least in part, to the generation of small molecule profiles of samples, cells, and cellular compartments. Small molecule profiles "fingerprint" the cell or cellular compartment and identify the presence, absence or relative quantity of small molecules. The small molecule profiles of the cells or cellular compartments may be obtained through, for example, a single technique or a combination of techniques for separating and/or identifying small molecules known in the art. Examples of separation and analytical techniques which can be used to separate and identify the compounds of the small molecule profiles include: HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art. Preferably, the methods of the invention detect both electrically neutral as well as electrochemically active compounds. Detection and analytical techniques can be arranged in parallel to optimize the number of molecules identified.

The term "small molecules" includes organic and inorganic molecules which are present in the cell, cellular compartment, organelle or extracellular space. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell. In one embodiment, the small molecules of the invention are isolated.

The term "metabolome" includes all of the small molecules present in a given organism. The metabolome includes both metabolites as well as products of catabolism.

The term "metabolomic marker" refers to a molecule selected by a comparison of small molecule profiles wherein the molecule is observed to increase or decrease responsive to the application of a stimuli, such as the application of a treatment regimen to a subject.

The language "small molecule profile" includes the inventory of small molecules in tangible form within a targeted cell, extracellular space, tissue, organ, organism, or any derivative fraction thereof, e.g., cellular compartment, that is necessary and/or sufficient to provide information to a user for its intended use within the methods described herein. The inventory would include the quantity and/or type of small molecules present. The ordinarily skilled artisan would know that the information which is necessary and/or sufficient will vary depending on the intended use of the "small molecule profile." For example, the "small molecule profile," can be determined using a single technique for an intended use but may require the use of several different techniques for another intended use depending on such factors as the disease state involved, the types of small molecules present in a particular targeted cellular compartment, the cellular compartment being assayed per se., etc.

The relevant information in a "small molecule profile" also may vary depending on the intended use of the compiled information, e.g. spectra. For example for some intended uses, the amounts of a particular small molecule or a particular class of small molecules may be relevant, but for other uses the distribution of types of small molecules may be relevant.

The ordinarily skilled artisan would be able to determine the appropriate "small molecule profiles" for each method described herein by comparing small molecule profiles from diseased and/or test subjects with standard and/or healthy subjects. These comparisons can be made by individuals, e.g., visually, or can be made using software designed to make such comparisons, e.g., a software program may provide a secondary output which provides useful information to a user. For example, a software program can be used to confirm a profile or can be used to provide a read-out when a comparison between profiles is not possible with a "naked eye". The selection of an appropriate software program, e.g., a pattern recognition software program, is within the ordinary skill of the art. It should be noted that the comparison of the profiles can be done both quantitatively and qualitatively.

In certain embodiments, the invention includes a method of identifying disease-relevant small molecules. The method includes comparing changes in small molecule profiles of diseased cells, cellular compartments, extracellular spaces or organelles, both pre- and post-initiation of treatment to a standard profile or to a standard set of predetermined metabolomic markers. The method also involves identifying the small molecules which are present in aberrant amounts in the diseased small molecule profile. The small molecules present in aberrant amounts in the diseased cells are "disease-relevant small molecules."

The language "disease-relevant small molecules" includes both small molecules present in aberrant amount in diseased small molecule profiles and, in addition, small molecules which are potentially involved in disease initiation, progression or prediction. The language "aberrant levels" includes any level, amount, or concentration of a small molecule in a cell, cellular compartment, extracellular space or organelle which is different from the level of the small molecule of a standard sample.

The term "standard profile" includes profiles derived from healthy cells, advantageously from a similar origin as the source. In one embodiment, the standard profile is an average of many samples of a certain cell type and/or a certain cellular compartment. In another embodiment, the standard profile may be derived from a patient prior to the onset of the disease state or from cells not affected by the disease state. Or, in another embodiment the standard profile can be an average of the profiles obtained from numerous sources, e.g., the standard profile may be an average of small molecule profiles obtained from 2 or more subjects. The standard profile can be a small molecule profile of a certain cellular compartment or from a certain subset of cells. Advantageously, the small molecules with aberrant levels in the sample are identified, e.g., HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art. In one embodiment, the small molecule profile of the sample, cell, or cellular compartment, is compared to the standard profile by using subtracting one profile from the other. Standard profiles can also be made of the effects of certain agents (e.g., drugs, therapeutic agents, toxins, etc.) on both healthy and diseased cells (e.g., cells diseased with the type of disease treated by the therapeutic agent).

In another aspect, the invention pertains to the comparison of small molecule profiles of cells, cellular compartments, organelles, or extracellular material with those of cells, cellular compartments, organelles, or extracellular material treated with toxins, chemical agents or therapeutic agent (or derived from an organism treated with the agent or drug). In one embodiment, the cells, cellular compartments, organelles, or extracellular material are diseased (or derived from a diseased organism) and are treated with a therapeutic agent which is known to modify or treat that disease. For example, the small molecule profile of a cell treated with a therapeutic agent, chemical agent, or toxin, can be compared the small molecule profile of a normal cell, e.g., a healthy cell of similar lineage, or a diseased cell of similar lineage which was not treated with the therapeutic agent, chemical agent, or toxin.

In addition, subtraction profiles can be obtained by subtracting the non-treated profile or a standard profile with the small molecule profile from a treated cell, cellular compartment, organelle, or extracellular fluid. The subtraction profiles can then be used to identify certain small molecules the presence or the absence of which may indicate the efficacy or the toxicity of the compound. The subtraction profiles can be made using, for example, computer programs known to those of skill in the art, e.g., pattern recognition software program. It should be noted that the comparison of the profiles can be done both quantitatively and qualitatively.

In a further embodiment, the invention pertains to certain small molecules which indicate the efficacy or the toxicity of the compound. The invention also applies to assays which can be developed to indicate the presence or absence of these certain small molecules. For example, if the presence of a certain small molecule is essential for the efficacy of a particular therapeutic compound, then an assay can be developed to quickly determine the presence or absence of this certain small molecule in cell samples treated with test compounds. This can be both an effective and inexpensive method to determine the potential efficacy of compounds. It can be used alone or in combination with traditional drug screening assays such as, for example, binding assays and other enzymatic assays.

For example, in search of molecules with anti-mycobacterial activity, small molecule profiles could be taken of cells at certain intervals after being treated with a known anti-mycobacterial drug (e.g INH, rifampin, rifalazil, etc.). Comparison of the small molecule profiles of these cells could lead to the identification of small molecules regulated by these drugs. The identified small molecules could then be used to guide drug discovery by pointing to pathways which could be targeted for drug design or by using them as therapeutic or nutriceutical agents.

In the context of this invention, anti-mycobacterial agents, or compounds that enhance the effects of such agents, include, for example: isoniazid, rifampin, rifalazil ethambutol, pyrazinamide, amikacin, moxifloxacin, ciprofloxacin, ofloxacin, kanamycinm, levofloxacin, ethambutol, aminosalicyclic acid, rifapentine, cycloserine, ethionamide, capreomycin, gatifloxacin, viomycin, envyomicin and combinations thereof.

In a preferred embodiment, the subject is a human in need of treatment for infection wherein the *Mycobacterium* species is preferably *Mycobacterium tuberculosis, Mycobacterium abscessus*, and *Mycobacterium paratuberculosis*. However, it is contemplated that the methodology taught herein will be applicable to assess the efficacy of anti-mycobacterial treatment for infections from additional Mycobacterium species including, but not limited to, *M. abscessus, M. africanum, M. agri, M. aichiense, M. alvei, M. arosiense, M. arupense, M. asiaticum, M. aubagnense, M. aurum, M. austroafricanum, Mycobacterium avium* complex (MAC): *M. avium, M. avium paratuberculosis, M. avium silvaticum, M. avium* "hominissuis", *M. colombiense, M. boenickei, M. bohemicum, M. bolletii, M. botniense, M. bovis, M. branderi, M. brisbanense, M. brumae, M. canariasense, M. caprae, M. celatum, M. chelonae, M. chimaera, M. chitae, M. chlorophenolicum, M. chubuense, M. conceptionense, M. confluentis, M. conspicuum, M. cookii, M. cosmeticum, M. diernhoferi, M. doricum, M. duvalii, M. elephantis, M. fallax, M. farcinogenes, M. flavescens, M. florentinum, M. fluoroanthenivorans, M. fortuitum, M. fortuitum subsp. acetamidolyticum, M. frederiksbergense, M. gadium, M. gastri, M. genavense, M. gilvum, M. goodii, M. gordonae, M. haemophilum, M. hassiacum, M. heckeshornense, M. heidelbergense, M. hiberniae, M. hodleri, M. holsaticum, M. houstonense, M. immunogenum, M. interjectum, M. intermedium, M. intracellulare, M. kansasii, M. komossense, M. kubicae, M. kumamotonense, M. lacus, M. lentiflavum, M. leprae, M. lepraemurium, M. lepromatosis, M. madagascariense, M. mageritense, M. malmoense, M. marinum, M. massiliense, M. microti, M. monacense, M. montefiorense, M. moriokaense, M. mucogenicum, M. murale, M. nebraskense, M. neoaurum, M. neworleansense, M. nonchromogenicum, M. novocastrense, M. obuense, M. palustre, M. parafortuitum, M. parascrofulaceum, M. parmense, M. peregrinum, M. phlei, M. phocaicum, M. pinnipedii, M. porcinum, M. poriferae, M. pseudoshottsii, M. pulveris, M. psychrotolerans, M. pyrenivorans, M. rhodesiae, M. saskatchewanense, M. scrofulaceum, M. senegalense, M. seoulense, M. septicum, M. shimoidei, M. shottsii, M. simiae, M. smegmatis, M. sphagni, M. szulgai, M. terrae, M. thermoresistibile, M. tokaiense, M. triplex, M. triviale, Mycobacterium tuberculosis* complex (MTBC), members: *M. bovis, M. bovis BCG, M. africanum, M. canetti, M. caprae, M. pinnipedii, M. tusciae, M. ulcerans, M. vaccae, M. vanbaalenii, M. wolinskyi,* and *M. xenopi*.

Samples useful for the screening methods above include bodily fluids that are likely to include product released by the mycobacterial bacilli or infected host tissue, such as, blood, mucus, phlegm, sputum, pus, lung biopsy, etc.

When agents disclosed herein or determined by a screening method disclosed herein are provided to a subject, the agents can be provided in a pharmaceutically acceptable form or composition. By "pharmaceutically acceptable" is meant a material that is not biologically or otherwise undesirable, and which can be administered to an individual along with the selected substrate without causing significant undesirable biological effects or interacting in a deleterious manner with any of the other components of the pharmaceutical composition in which it is contained.

Further provided is a method of making an agent that modulates the activation state of a *Mycobacterium* species involving identifying an agent using one of the screening methods disclosed herein and making a pharmaceutically acceptable dosage form for providing to a patient that includes the dosage form. Dosage forms created by this method can also be packaged in individual or multiple dosage forms. Such packaging can maintain the viability and efficacy of the dosage form.

Pharmaceutical compositions containing agents disclosed herein or identified using methods disclosed herein can be prepared by mixing the desired agents with an appropriate vehicle suitable for the intended route of administration, optionally for use in an appropriate drug delivery device. In making pharmaceutical compositions, the agents can be mixed with an excipient, diluted by an excipient or enclosed within such a carrier which can be in the form of a capsule, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, elixirs, suspensions, emulsions, solutions, syrups, aerosols (as a solid or in a liquid medium), ointments containing, for example, up to 10% by weight of the therapeutic agents, soft and hard gelatin capsules, suppositories, sterile injectable solutions, and sterile packaged powders.

Some examples of suitable excipients include artificial biological fluid, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl- and propylhydroxy-benzoates; sweetening agents; and flavoring agents. The agents disclosed herein or identified using methods disclosed herein can be formulated so as to provide quick, sustained or delayed release of the agents after administration to the subject by employing procedures known in the art.

For preparing solid compositions such as tablets, an agent is mixed with a pharmaceutical excipient to form a solid preformulation composition containing a homogeneous mixture of the agent. When referring to these preformulation compositions as homogeneous, it is meant that the agents are dispersed evenly throughout the composition so that the composition may be readily subdivided into equally effective unit dosage forms such as tablets, pills and capsules. These tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the agents disclosed herein or identified using methods disclosed herein may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine.

Solution, suspension, or powder compositions may be administered, preferably orally or nasally, from drug delivery devices which deliver the formulation in an appropriate manner. Another formulation employed in the methods described herein employs transdermal delivery devices ("patches"). Such transdermal patches may be used to provide continuous or discontinuous infusion of the therapeutic agents in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents. Other suitable formulations for use with the agents described herein can be found in Remington's Science and Practice of Pharmacy, 21st Edition, ed. University of the Sciences in Philadelphia, Lippincott, Williams & Wilkins, Philadelphia Pa., 2005.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The examples below are intended to further illustrate certain embodiments of the invention, and are not intended to limit the scope of the claims.

Example 1

Detailed Materials and Methods for the Initial Identification of Metabolites from Urine Samples Clinical Samples.

All the urine samples were procured from Tuberculosis Research Unit (TBRU) Specimen Repository which was collected during two separate clinical trials conducted in Uganda. The first set of samples (from 21 individuals) originated from TBRU IL-2 study [Johnson J L et al., Am. J. Respir. Crit Care Med. (2003) 168:185-191] and the second set of samples (14 individuals) was from TBRU-TBTC study NAA2M. These samples were from adult pulmonary cavitary tuberculosis patients of both sexes with or without HIV co-infection. The samples were at the initial time of TB diagnosis (before start of therapy, D0) and at two weeks (W2), four weeks (W4), eight weeks (W8) and six months of treatment (M6). Urine specimens were stored at −80° C. upon collection and were sterilized by γ-irradiation before analysis for safety reasons.

Liquid Chromatography-Mass Spectrometry (LC-MS) Analysis of Urine Samples.

The creatinine concentrations of the urine specimens were determined by the alkaline picrate method using a creatinine assay kit from Oxford Biomedical Research (Oxford, Mich.). The urine samples were clarified by centrifugation and subjected to liquid chromatography-mass spectrometry (LC-MS). An aliquot of urine containing 13 μg of creatinine was applied to a Waters X-Bridge or Atlantis T3 reverse-phase $C_{18}$ column 3.5 μm (2.1×150 mm) that was connected to an Agilent 1200 series HPLC system. The metabolites were eluted with a 0 to 80% linear gradient of methanol in 0.1% formic acid at a flow rate of 320 μl/min. The eluate was introduced directly into an Agilent 6220 Accurate-Mass TOF or Agilent 6250 Q-TOF mass spectrometer equipped with an Agilent multimode source with simultaneous electrospray ionization and atmospheric pressure chemical ionization capability. The positive-ion MS data were collected using Agilent MassHunter work station software. These MS data were processed with the molecular feature extractor algorithm (MFE) in Agilent MassHunter Qualitative Analysis software to identify molecular features (compounds with a defined exact mass and retention time) present in each sample. A preset minimum abundance (100 counts) was used as a cutoff to filter out extremely low abundance molecular features. The data from different sample groups (i.e. treatment time points) were compared using either Agilent GeneSpring MS or Agilent Mass Profiler software. The molecular features present in at least 70% of the samples in a given group and present at a concentration deemed suitable by the software for reliable quantitative analysis were selected. The relative abundance of these filtered molecular features obtained from different treatment time points were compared and features that vary significantly (at least 2.5 fold) in relative abundance between treatment groups were further analyzed to identify the metabolite structure. FIG. 3 presents a general overview of the steps of data analyses to extract relevant molecular features and to compare these across large data sets.

Gas Chromatography-Mass Spectrometry (GC-MS) Analysis of the Urine Samples.

For GC-MS analysis of the urinary metabolites, aliquots of urine samples containing 13 μg of creatinine were transferred to 13×100 mm glass culture tubes and 1 nmole of α-aminobutyric acid was added tube as an internal standard. The samples were dried under vacuum, 25 μl of pyridine and 25 μl of MTBSTFA with 1% TBDMCS were added and the sealed tubes were heated at 70° C. for 20 min. The tert-butyldimethylsilyl derivatives (1 μl) were injected directly to a Varian CP-3800 Gas Chromatograph fitted with a Varian FactorFour capillary column and a Varian 320-MS detector. Authentic reference compounds were also derivatized and analyzed by GC-MS following the same methods. Concentration curves of some of the identified metabolites were also prepared to determine the absolute concentration in urine samples.

Identification of the Metabolites.

Multiple molecular features increased in abundance following the onset of treatment and others decreased in abundance following the onset of treatment. The chemical formula of each differentiating molecular feature was predicted based on accurate mass data, and searched against the publicly available metabolite databases such as Human Metabolome Database (HMDB) [Wishart D S, et al., *Nucleic Acids Res.* (2007) 35: D521-D526] and METLIN database for potential structure identification. A number of the differentiating compounds were tentatively identified based on these searches. Comparison of mass spectrum, tandem mass spectrum and coelution with commercial reference compounds was used for positive identification of differentiating metabolites by LC-MS and GC-MS.

Example 2

Initial Identification of Metabolites from Urine Samples

Urine is a clinical sample that allows for non-invasive diagnostics. Potential biomarkers of several diseases have been discovered recently from the analyses of urine [Kim, K. et al., *Mol. Cell Proteomics.* 8, 558-570 (2009); Johnson, J. C. et al., *Clin. Gastroenterol. Hepatol.* 4, 1358-1365 (2006); Zhang H. et al., *Anal. Biochem.* 399, 302-304 (2010); Nam H. et al., *Bioinformatics.* 25, 3151-3157 (2009)]. The ability to identify such biomarkers is a result of the advancement in analytical techniques suitable for identification and quantification of chemicals at low concentrations from complex samples such as urine.

Urine contains a wide variety of metabolites. A vast majority of these urinary metabolites are below 1000 Daltons [Bollard, M. E., et al., *NMR Biomed.* 18, 143-162 (2005)]. LC-MS is well suited to analyze products of low molecular mass and is used extensively for metabolomic studies [Dettmer, K., et al., *Mass Spectrom. Rev.* 26, 51-78 (2007)]. Therefore, this analytical platform was chosen for the analysis of urine from TB patients. The relative abundance of the urinary metabolites varies depending on liquid intake, but the amount of creatinine excreted daily by an individual is relatively constant [Cone, E. J., et al., *J. Anal. Toxicol.* 33, 1-7 (2009)]. Thus, urinary creatinine levels were used to normalize the rate of excretion of other metabolites.

Figure 4:
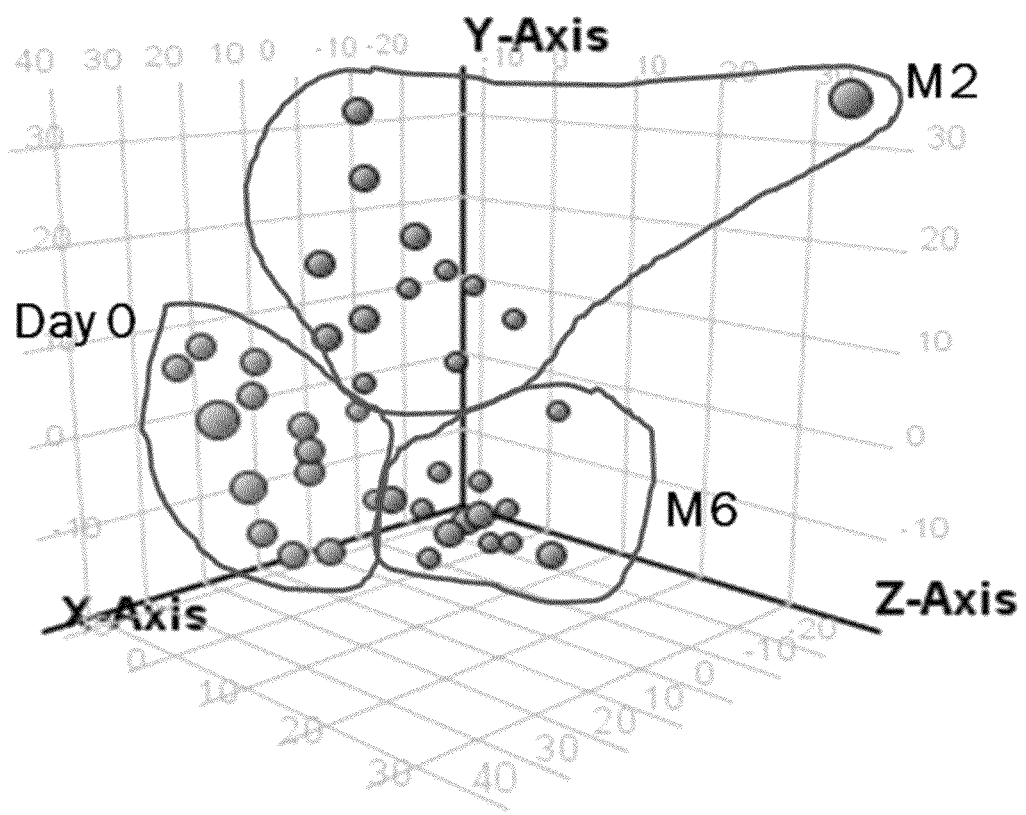
FIG. 4 is a 3D scatter plot showing PCA analysis of human urine from TB patients at day of diagnosis (cluster labeled "Day 0"), two month (cluster labeled "M2"), and six months (cluster labeled "M6") after the start of TB therapy where unique molecular features differed in abundance between time points in at least 70% of the patients.

The urinary metabolites in TB patients can vary due to other facts such as normal flora or diet. Additionally, metabolites can also vary depending the age, sex and HIV co-infection status of an individual. To eliminate these potentially confounding variables, Agilent Mass Profiler software was used to filter and limit comparative analyses only to those molecular features present in at least 70% of the samples for any given time point of treatment. To demonstrate that the individual sample groups would cluster based on the molecular features present in at least 70% of the samples for any given time point of treatment, unsupervised principal component analysis was performed on the day-0 ("D0"), week-8 ("W8"), and month-6 ("M6") data sets for fifteen patients from the TBRU MP study (FIG. 4). This evaluation showed strong separation of these groups and provided justification to identify those molecular features that allowed this separation. The LC-MS based metabolomics approach enabled the identification of compounds, showing changes in abundance during the course of treatment.

Urine samples (thirty-five patients in total) from the two clinical studies (MP and TBRU-TBTC NAA2M) were analyzed independently and the resultant data were consolidated to identify molecular features that showed similar patterns of change over the course of treatment out to W4. These consolidated lists of differentiating molecular features were divided into two major groups: products (molecular features) that increased in abundance following onset of treatment and molecular features that decreased in abundance with treatment. As a proof of principle, metabolites of anti-tuberculosis drugs in the group of compounds that displayed increased abundance over the course of treatment were also identified (data not shown).

Figure 5:
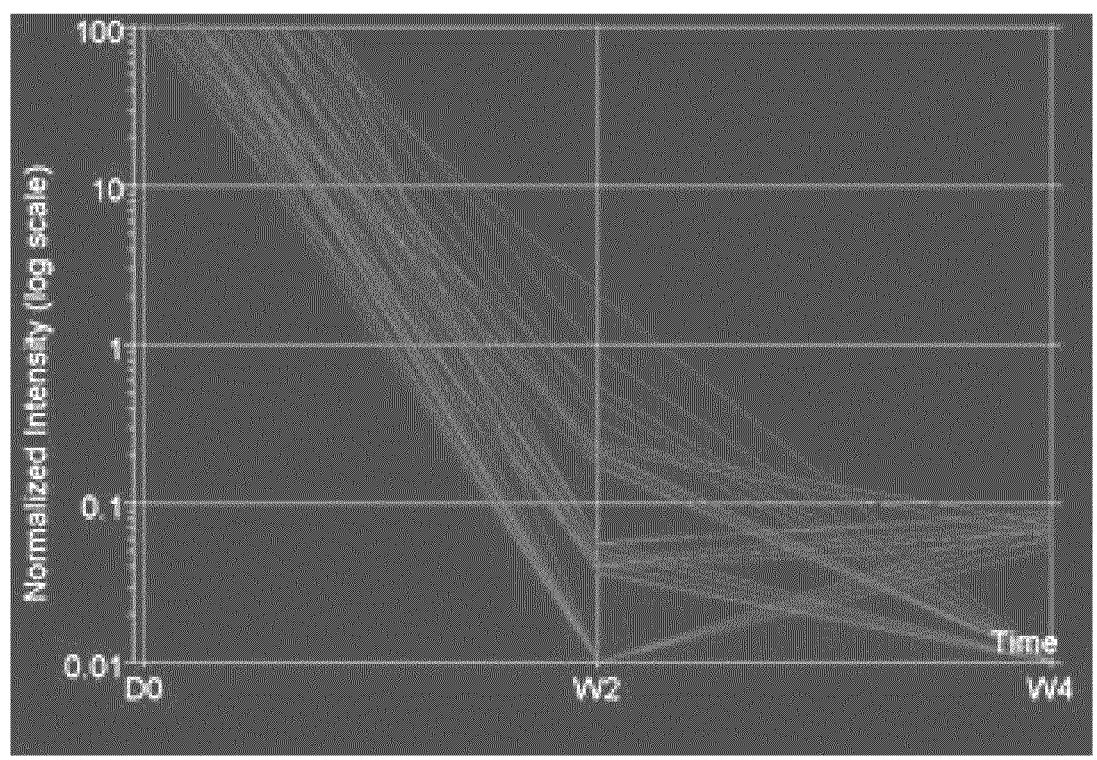
FIG. 5 is a graph showing that the molecular features identified by GeneSpring MS software as significantly reduced in abundance following treatment. The treatment duration (x-axis) is represented as weeks. The intensity of compounds represented in this graph is based on the arbitrary numbers used to calculate the area of the relevant peaks and does not represent actual concentrations of these molecular features.

The molecular features with decreased abundance following treatment onset were further divided into three groups based on the profile of change: a) compounds that rapidly decreased in abundance to a low but detectable level, b) compounds that rapidly decreased in abundance and increased slightly in abundance by W4 of treatment, and c) compounds that decreased in abundance rapidly and became undetectable by W4 (FIG. 5). In total fifty-eight molecular features that fell into one of these three categories were observed.

TABLE 1

Metabolites identified in the urine of tuberculosis patients and that decrease in abundance with successful anti-tuberculosis treatment.

| Compound # | Identified Biomarker | Formula | Mass |
|---|---|---|---|
| 1 | Hydroxyproline | $C_5H_9NO_3$ | 131.058243 |
| 2 | N-Acetyl-L-aspartic acid | $C_6H_9NO_5$ | 175.048065 |
| 3 | Dimethyl-L-arginine | $C_8H_{18}N_4O_2$ | 202.142975 |
| 4 | N-Acetylasparagine | $C_6H_{10}N_2O_4$ | 174.064056 |
| 5 | 1-Methylhistidine | $C_7H_{11}N_3O_2$ | 169.085129 |
| 6 | L-Phenylalanine | $C_9H_{11}NO_2$ | 165.078979 |
| 7 | 2,2,5,5-Tetramethyl-3-pyrrolidinecarboxamide | $C_9H_{18}N_2O$ | 170.141913 |
| 8 | Pyroglutamic acid | $C_5H_7NO_3$ | 129.042587 |
| 9 | Acetylcysteine | $C_5H_9NO_3S$ | 163.030319 |
| 10 | Trigonelline | $C_7H_7NO_2$ | 137.047684 |
| 11 | S-Adenosylhomocysteine | $C_{14}H_{20}N_6O_5S$ | 384.121582 |
| 12 | L-Tyrosine | $C_9H_{11}NO_3$ | 181.073898 |
| 13 | alpha-Aminoadipic acid | $C_6H_{11}NO_4$ | 161.068802 |
| 14 | Quinolinic acid | $C_7H_5NO_4$ | 167.021851 |
| 15 | Hypoxanthine | $C_5H_4N_4O$ | 136.038513 |
| 16 | Pyrroline hydroxycarboxylic acid | $C_5H_7NO_3$ | 129.042587 |

The molecular formula of each molecular feature was determined based on accurate mass data, and searched against the Human Metabolome Database and METLIN database for potential structure identification. A number of the differentiating compounds were tentatively identified based on these searches and sixteen metabolites were positively identified using authentic reference compounds (Tables 1 and 2). Among the identified metabolites, several are reportedly associated with inflammatory responses, but others have no known association with any infectious disease. Amino acids such as hydroxyproline are likely associated with collagen damage resulting from the infection and have been reported previously [Pawelec, D. [Urinary excretion of hydroxyproline in tuberculous patients]. *Gruzlica.* 40, 913-918 (1972); Lysov, A. V. et al., *Probl. Tuberk. Bolezn. Legk.* 11-13 (2003)]. Abnormal pyroglutamic acid metabolism has been reported from tuberculosis patients, but the reason for this change is unknown [Vinnik, L. A. et al., *Probl. Tuberk.* 50, 67-72 (1972)]. Of the fifty-eight differentiating molecular features, thirty-nine did not provide a database match or were matched to a larger list of structures assigned to a predicted molecular formula. Further studies will identify the exact structure of these molecular features. Thus, the present results demonstrate metabolic markers associated with TB in humans can be identified. Moreover, these new biomarkers can be used to predict treatment outcome and the large number of differentiating molecular features identified allow for the selection of novel arrays of biomarkers for primary diagnosis of tuberculosis.

TABLE 2

Identified molecular features decreased in abundance following treatment.

| Compound # | Identified Biomarker | Nature of the Change |
|---|---|---|
| 1 | Hydroxyproline | Down by W2 then increase slightly |
| 2 | N-Acetyl-L-aspartic acid | Down by W2 then increase slightly |
| 3 | Dimethyl-L-arginine | Down gradually |
| 4 | N-Acetylasparagine | Down by W2 and then steady |
| 5 | 1-Methylhistidine | Down gradually |
| 6 | L-Phenylalanine | Down by W2 then increase slightly |
| 7 | 2,2,5,5-Tetramethyl-3-pyrrolidinecarboxamide | Down by W2 and then steady |
| 8 | Pyroglutamic acid | Down by W2 and then steady |
| 9 | Acetylcysteine | Down gradually |
| 10 | Trigonelline | Down by W2 then increase slightly |
| 11 | S-Adenosylhomocysteine | Down gradually |
| 12 | L-Tyrosine | Down by W2 and then steady |
| 13 | alpha-Aminoadipic acid | Down by W2 and then steady |
| 14 | Quinolinic acid | Down gradually |
| 15 | Hypoxanthine | Down by W2 then increase slightly |
| 16 | Pyrroline hydroxycarboxylic acid | Down gradually |

Example 3

Detailed Analyses of Urine Samples

Methods for the analysis of human metabolites in urine and plasma/serum were developed and applied to the evaluation of tuberculosis patient samples over the course of treatment. Specifically, urine samples from the initial day of diagnosis ("day-0") and two weeks, four weeks or eight weeks, and six months during treatment were assessed and compared with respect to their metabolomic profiles. The standard approach was to normalize the urine samples based the creatinine concentration as estimated by a colorimetric assay kit (Oxford Biochemical Research). Once clinical specimens were processed, aliquots (5-10 μl) were analyzed by LC/MS using an Agilent 6500 qTOF instrument interfaced with an Agilent 1200 HPLC system containing a Waters Atlantis Reversed Phase column or Waters X-bridge $C_{18}$ column. The MS data obtained was processed using the Molecular Feature Extractor of the Mass Hunter Workstation software (Agilent) to generate a file of molecular features. Each molecular feature is defined by its accurate mass and retention time. The intensity of its mass signal also provides a relative abundance. The molecular feature data was subsequently analyzed using the Agilent Mass Profiler Pro software. The Mass Profiler software allowed for principle component analysis (PCA) to demonstrate whether there was a large enough change in the profile of molecular features to differentiate between the treatment groups and time points.

Figure 6:
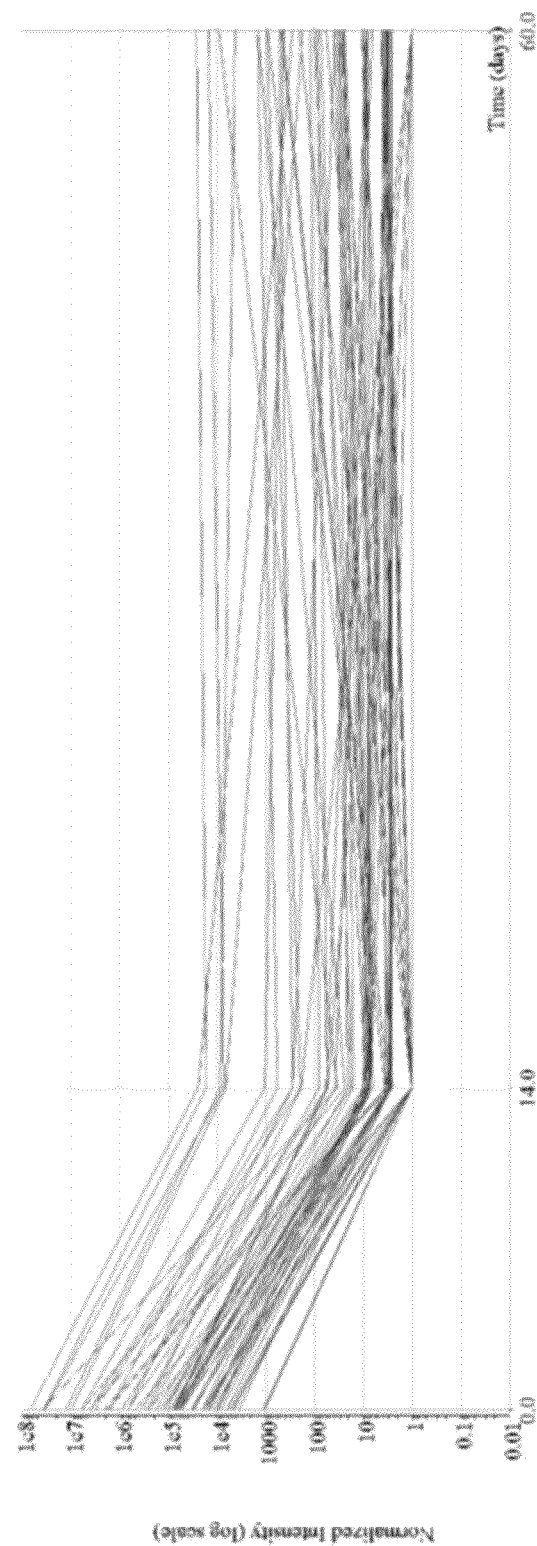
FIG. 6 is a graph showing that the molecular features identified by Mass Profiler Pro software as being significantly "down regulated" following the start of anti-TB treatment. The treatment duration represented as days. The intensities of compounds represented in the graph are based on the arbitrary numbers used to calculate the area of the relevant peaks and do not represent actual molecular concentrations.
Figure 7:
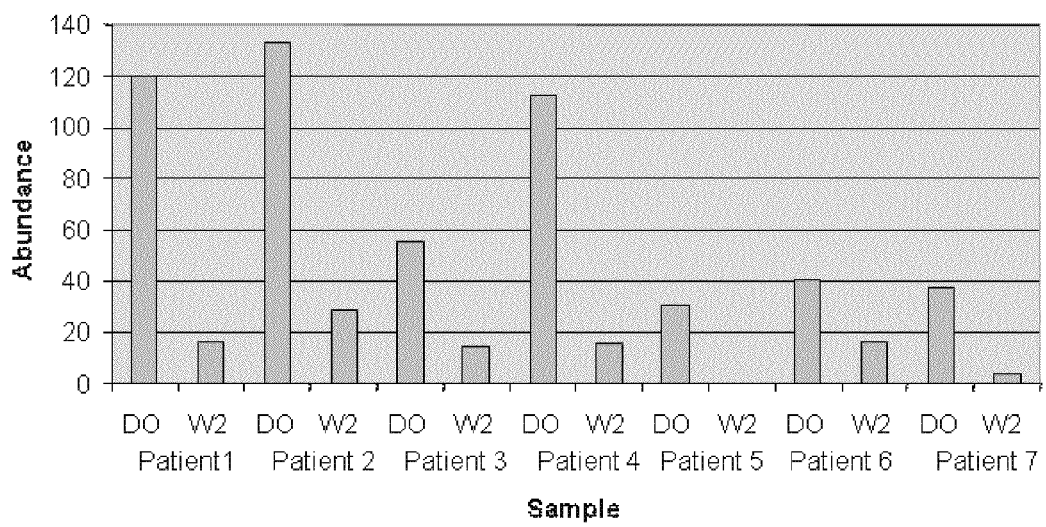
FIG. 7 is a histogram illustrating the evaluation of the quantitative difference in pyroglutamate between day-0 ("D0") and two week urine samples of randomly selected patients.

FIG. 4 provides the results of a PCA of MS data from urine samples of TB patients at the day-0, two months (M2), and six months (M6) after the start of standard anti-TB treatment. The Mass Profiler Pro software also allowed for the selection/identification of molecular features that present a specific profile change over time (FIG. 6).

These types of statistical analyses allowed for the generation of a list of molecular features, with each feature defined by an experimentally determined accurate molecular mass, providing a biosignature of specimens at different points during treatment. Accurate molecular masses also provided the ability to predict chemical formulas that were queried against METLIN at Scripps Center for Mass Spectrometry, and the Human Metabolome Database (HMDB) [Smith C A, et al., *Ther Drug Monit.* 2005; 27(6):747-51; Wishart D S, et al., *Nucleic Acids Res.* 2009; 37(Database issue): D603-10. PMCID: 2686599] to determine the molecular identities. The identities of individual molecular features were confirmed by comparative analysis of MS/MS fragmentation patterns of the product in the experimental samples with that of a reference compound, and/or analysis by gas chromatography (GC)/MS. This overall approach led to the identification of sixteen urine metabolites that significantly decrease in abundance by two weeks after the start of anti-tuberculosis therapy and correlate with successful treatment. The sixteen urine metabolites are presented in Table 1 (above).

Of interest with regard to the use of LC/MS in metabolomic studies is its ability to accurately quantify individual products in comparison to other methods such as GC/MS or NMR [Smilde A K, et al., *Metabolomics.* 2010; 6(1):3-17. PMCID: 2834778]. While this can be used as an advantage to define those products with the greatest degree of change between time points or disease states, alternative strategies can be used to confirm that differences observed by LC/MS could also be observed with other methodologies. Thus, for a randomly selected group of patients, day-0 and two week urine samples were subjected to N-(t-butyldimethylsilyl)-N-methyltrifluoroacetamide (MTBSTFA) derivatization and analyzed by GC/MS using the appropriate standard to confirm identity and an internal standard for quantification. As shown in FIG. 5, the differences detected for pyroglutamate by LC/MS were corroborated by GC/MS of the MTBSTFA derivative. This type of quantifiable conformation was performed for a number of the compounds listed in Table 1, and was successful for each compound tested.

Table 3 presents a summary of the urine samples obtained and analyses performed to date.

TABLE 3

Urine samples obtained and analyses performed.

| Date | Sample Set | Number (#s) | Time Points | LC/MS Analysis | Data Analysis |
|---|---|---|---|---|---|
| April 2008 | TBRU Pilot Project | 20 | D0, 2W, 2M, 6M | Yes all time points | Yes all time points |
| April 2009 | NAA2m Set 1 | 14 | D0, 2W, 1M, 4M and 1M | Yes all for D0, 2W, and 1M | Yes for D0, 2W, and 1M |
| February 2010 | Stellenbosch | 40 | D0, 2W, 1M, 6M | Yes all time points | Yes for D0, 2W, and 6M |
| October 2010 | NAA2m Set 2 | 22 | D0, 2W, 1M, 1.5M, 2M, 3M, 4M, 7M, 8M, 9M | No | No |

Figure 8:
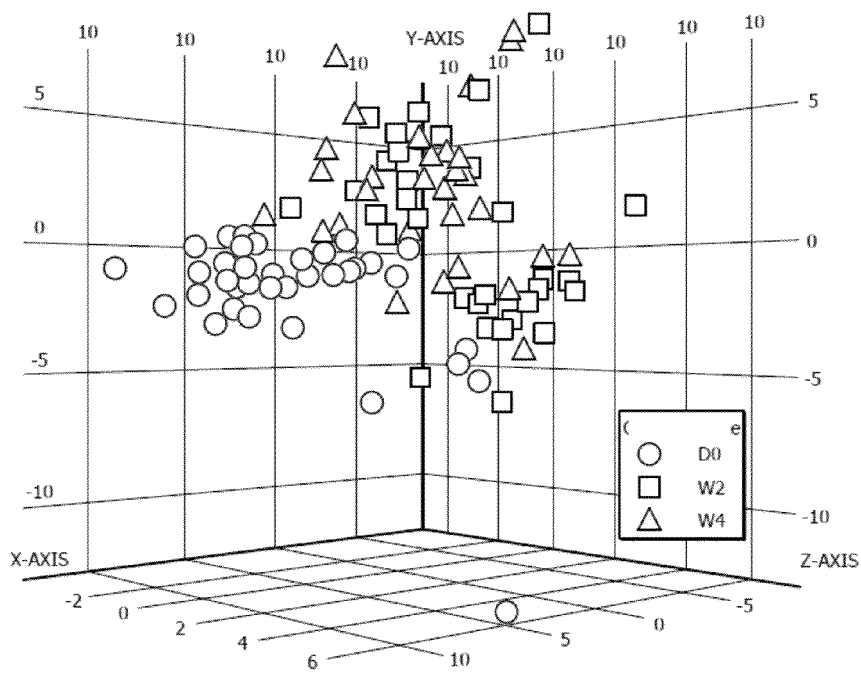
FIG. 8 is a 3D scatter plot of the PCA analysis of metabolomic data from Stellenbosch urine samples.

FIG. 8 shows the PCA analysis of metabolomic data from Stellenbosch urine samples. Table 4 provides data on the validation of the signature with the Stellenbosch sample set.

TABLE 4

Validation of signature with the Stellenbosch sample set.

| Observed Accurate Mass | Calculated Formula | Identified Biomarker | Compound #* |
|---|---|---|---|
| 129.0434 | C5H7NO3 | Pyroglutamic acid | 8 |
| 135.0687 | C5H11O4 | | |
| 137.0401 | C7H7NO2 | Trigonelline | 10 |
| 159.126 | C8H17NO2 | | |
| 167.0225 | C8H7O4 | Quinolinic acid | 14 |
| 169.0854 | C7H11N3O2 | 1-Methylhistidine | 5 |
| 170.1421 | C9H18N2O | 2,2,5,5-Tetramethyl-3-pyrrolidinecarboxamide | 7 |
| 174.0639 | C6H10N2O4 | N-Acetylasparagine | 4 |
| 175.048065 | $C_6H_9NO_5$ | N-Acetyl-L-aspartic acid | 2 |
| 181.0753 | C9H11NO3 | L-Tyrosine | 12 |
| 202.143 | C8H18N4O2 | Dimethyl-L-arginine | 3 |
| 221.0729 | C8H15NO4S | | |
| 234.1221 | C11H14N4O2 | | |
| 257.1014 | C10H15N3O5 | | |
| 263.1127 | C10H13N7O2 | | |
| 268.0942 | C14H20OS2 | | |
| 272.1014 | C12H12N6O2 | | |
| 282.0267 | C6H10N4O7S | | |
| 293.1048 | C10H19N3O5S | | |
| 301.1524 | C14H23NO6 | | |
| 338.1342 | C18H17NO5 | | |

*See Table 2 for corresponding compound #.

Samples analyzed in these studies were collected from patients receiving a standard regimen of INH, RIF, EMB, and PZA. Metabolites for each of these drugs could be detected in the urine samples collected after the start of therapy, but not in the urine collected at day-0, except for in two patients who had detectable amounts of drug metabolites at the day-0 time point. Based on those findings the urine samples from these two patients were removed from further analyses. These findings demonstrate that, in addition to monitoring changes in the biochemistry of the system, analyses as taught herein are able to monitor treatment compliance using the same samples with the applied methodology.

Example 4

Analyses of Serum Samples

Figure 9:
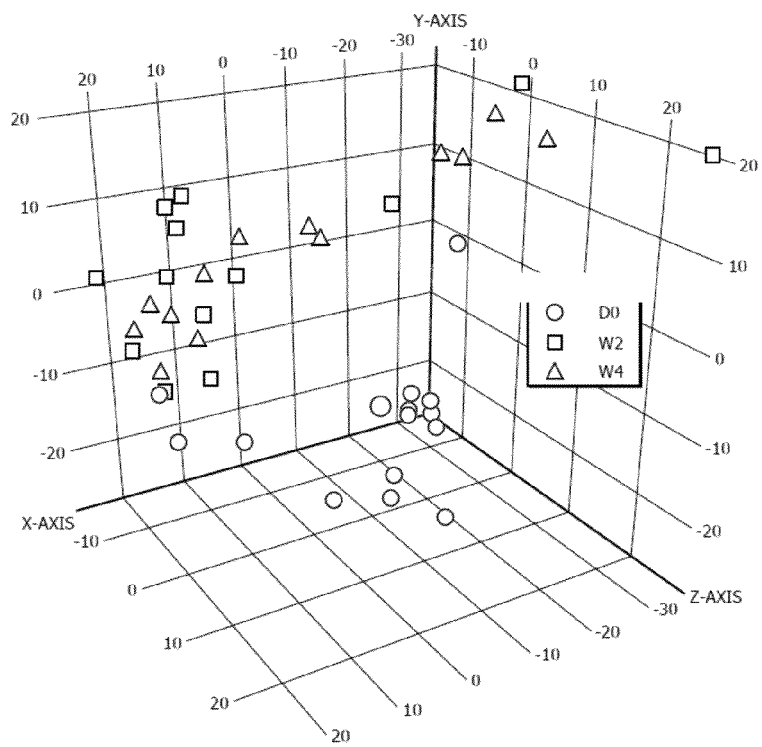
FIG. 9 is a 3D scatter plot of the PCA analysis of metabolomic data from the NAA2m Set 1 samples.

Analyses of plasma from forty-four tuberculosis patients in South Africa were performed to demonstrate that LC/MS-based metabolomic biomarker discovery for tuberculosis could be applied to plasma or serum samples (FIG. 9). Specifically, plasma from patients at day-0 and one month after the start of treatment were analyzed to validate the methodology. The inquiry focused on whether abundant products were present in at least 80% of the patients' samples at day-0 and, further, whether those products decreased significantly (p value<0.05) in the one month samples. The analysis provided a list of thirty-three molecular features that decreased in abundance between day-0 (also referred to as "D0") and one month of treatment by 9.81 to 69.75 fold. The thirty-three molecular features are presented in Table 5.

TABLE 5

Molecular features of plasma that decrease with tuberculosis treatment.

| Compound # | Mass | Predicted Chemical Formula | p-value | Fold Decrease in Abundance |
|---|---|---|---|---|
| 1 | 109.0017 | ND* | 5.80E−04 | 34.32 |
| 2 | 147.0532 | $C_5H_9NO_4$ | 1.23E−03 | 37.51 |
| 3 | 166.0483 | $C_6H_{14}OS_2$ | 2.67E−05 | 28.95 |
| 4 | 183.1619 | $C_{11}H_{21}NO$ | 1.25E−02 | 11.19 |

TABLE 5-continued

Molecular features of plasma that decrease with tuberculosis treatment.

| Compound # | Mass | Predicted Chemical Formula | p-value | Fold Decrease in Abundance |
|---|---|---|---|---|
| 5 | 206.0253 | $C_8H_{14}S_3$ | 3.70E-04 | 13.05 |
| 6 | 267.2564 | $C_{17}H_{33}NO$ | 5.93E-04 | 52.84 |
| 7 | 277.2405 | $C_{18}H_{31}NO$ | 1.15E-02 | 16.00 |
| 8 | 279.6151 | ND | 2.48E-03 | 12.90 |
| 9 | 280.044 | $C_{11}H_{20}S_4$ | 5.41E-04 | 11.64 |
| 10 | 281.2725 | $C_{18}H_{35}NO$ | 1.18E-02 | 33.20 |
| 11 | 295.252 | $C_{18}H_{33}NO_2$ | 1.07E-02 | 19.41 |
| 12 | 357.9725 | $C_8H_8C_{12}N_4O_8$ | 5.43E-06 | 69.75 |
| 13 | 388.1041 | $C_{18}H_{28}OS_4$ | 1.37E-04 | 16.61 |
| 14 | 406.0682 | $C_{18}H_{11}ClN_8O_2$ | 1.56E-03 | 15.01 |
| 15 | 410.7501 | ND | 1.59E-03 | 12.70 |
| 16 | 428.0801 | $C_{22}H_{13}ClN_6O_2$ | 3.61E-04 | 11.25 |
| 17 | 444.1124 | $C_{21}H_{32}S_5$ | 1.53E-04 | 26.64 |
| 18 | 463.306 | ND | 2.59E-03 | 13.18 |
| 19 | 499.0026 | $C_{12}H_{24}Cl_3N_7S_4$ | 6.05E-05 | 18.00 |
| 20 | 504.2774 | $C_{26}H_{40}N_4O_4S$ | 3.06E-03 | 11.76 |
| 21 | 534.2482 | $C_{30}H_{38}N_4OS_2$ | 5.74E-06 | 60.81 |
| 22 | 545.2994 | $C_{30}H_{43}NO_8$ | 2.74E-05 | 36.92 |
| 23 | 557.2901 | ND | 1.28E-03 | 16.18 |
| 24 | 609.3026 | ND | 8.98E-04 | 20.67 |
| 25 | 654.3719 | $C_{38}H_{58}N_2OS_3$ | 3.52E-04 | 10.54 |
| 26 | 696.5187 | $C_{41}H_{76}O_4S_2$ | 2.60E-05 | 17.14 |
| 27 | 742.4264 | $C_{50}H_{62}OS_2$ | 4.20E-05 | 21.68 |
| 28 | 799.5731 | ND | 1.83E-04 | 20.55 |
| 29 | 805.2392 | ND | 2.11E-03 | 9.81 |
| 30 | 817.5827 | ND | 4.58E-03 | 13.63 |
| 31 | 850.3915 | ND | 3.79E-04 | 14.38 |
| 32 | 859.6566 | ND | 1.74E-05 | 16.53 |
| 33 | 866.3661 | ND | 8.82E-08 | 62.54 |

*ND - There was more than one possible chemical formula for the exact mass.

Figure 10:
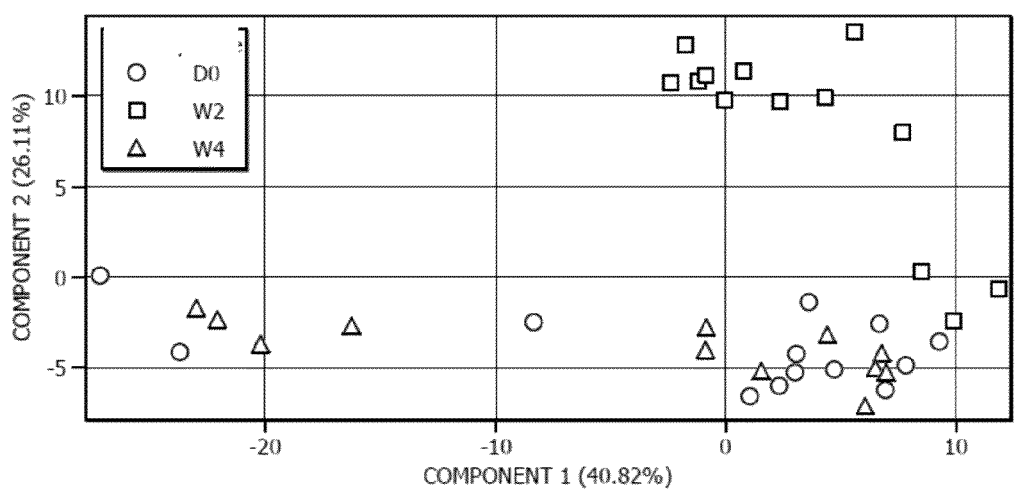
FIG. 10 is a 2D-PCA analysis of metabolomic data derived from urine samples from the NAA2m Set 1 samples.
Figure 11:
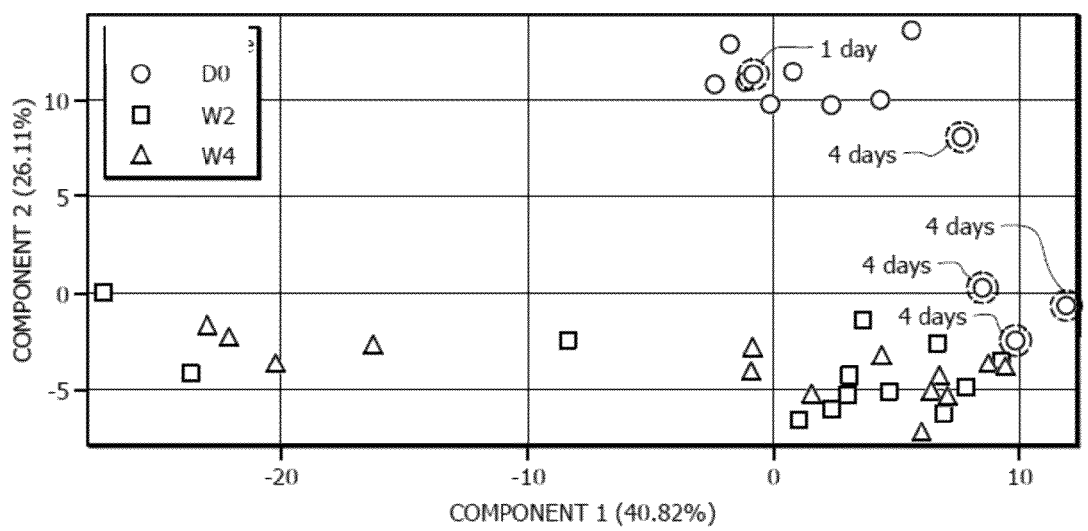
FIG. 11 re-presents the 2D-PCA analysis of FIG. 11 highlighting samples with previous anti-TB treatment.

Methodologies have been developed, as disclosed herein, to analyze metabolites of urine and plasma/serum by LC/MS and to extract the qualitative and quantitative information allowing for the comparison of large data sets, and identification of molecular features that provide a signature to distinguish between different sample sets (FIG. 10 and FIG. 11).

TABLE 6

Serum/plasma samples obtained with matched urine.

| Date | Sample Set | Number | Sera Obtained | Time Points |
|---|---|---|---|---|
| April 2009 | NAA2m Set 1 | 14 | Yes | D0, 2W, 1M, 4M |
| February 2010 | Stellenbosch | 40 | Yes | D0, 2W, 1M, 6M |
| October 2010 | NAA2m Set 2 | 22 | No, but it is available through CWRU | D0, 2W, 1M, 1.5M, 2M, 3M, 4M, 7M, 8M, 9M |

*NAA2m Set 1 and Stellenbosch sera/plasma will be used to develop metabolic signature for treatment.

The data and methodologies taught herein can be expanded to allow for the identification and validation of additional metabolite-based biosignatures to that further distinguish tuberculosis patients successfully responding to treatment from those that are not responding. To allow for the broader implementation of biosignatures in clinical trials, and ultimately patient care, the clinical specimens used to define the biosignatures can be selected from increasingly broad, well-defined populations that encompass the different variables associated with tuberculosis.

Additional clinical samples can be processed, analyzed by LC/MS, and the data processed to a point that identifies the most useful biosignatures for cure and treatment failure. This can be extended to allow for the comingling and cross-validation of data obtained with specimens of different clinical trials, providing for the most robust set of metabolites to be included as part of a biosignature. Additionally, an iterative process can be used to define patient subpopulations that do not adhere to current biosignatures, and then identify the appropriate clinical study that can provide the clinical samples that fill the gap for the specific patient subpopulation.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

TABLE 10

Molecular features that decreased in abundance following treatment.

| Observed Accurate Mass | Calculated Formula | Observed Accurate Mass | Calculated Formula |
|---|---|---|---|
| 126.1162 | C7H14N2 | 234.1221 | C11H14N4O2 |
| 129.0434 | C5H7NO3 | 239.0781 | C11H13NO5 |
| 131.057 | C5H9NO3 | 241.1539 | C10H19N5O2 |
| 135.0687 | C5H11O4 | 245.098 | C10H11N7O/C9H15N3O5 |
| 136.0395 | C5H4N4O | 248.1002 | C9H16N2O6 |
| 137.0401 | C7H7NO2 | 257.1014 | C10H15N3O5 |
| 142.127 | C6H14N4 | 258.147 | C13H14N4O2 |
| 143.1314 | C7H16N2O | 263.1127 | C10H13N7O2 |
| 149.0116 | C7H3NO3 | 266.0519 | C6H10N4O8 |
| 159.126 | C8H17NO2 | 268.0942 | C14H20OS2 |
| 161.0692 | C6H11NO4 | 272.1014 | C12H12N6O2 |
| 161.0825 | C10H11NO | 282.0267 | C6H10N4O7S |
| 165.0428 | C8H7NO3 | 282.1576 | C14H22N2O4 |
| 165.0795 | C9H11NO2 | 283.1282 | C11H17N5O4 |
| 167.0225 | C8H7O4 | 286.1284 | C11H18N4O5 |
| 167.033 | C6H5N3O3 | 293.1048 | C10H19N3O5S |
| 168.0286 | C5H4N4O3 | 294.0599 | C11H10N4O6 |
| 169.0854 | C7H11N3O2 | 295.1037 | C14H17NO6 |
| 170.1421 | C9H18N2O | 301.1524 | C14H23NO6 |
| 173.9949 | C7H11N3O2 | 308.091 | C16H12N4O3 |
| 174.0639 | C6H10N2O4 | 327.1069 | C18H17NO5 |
| 175.0485 | C6H9NO5/C7H5N5O | 338.1342 | C18H17NO5 |
| 181.0753 | C9H11NO3 | 345.0475 | C16H11NO8 |
| 182.1054 | C9H14N2O2 | 350.1511 | C14H26N2O6S |
| 202.143 | C8H18N4O2 | 370.165 | C14H22N6O6 |
| 203.1269 | C8H17N3O3 | 384.122 | C14H20N6O5S |
| 214.0094 | C8H6O7 | 405.1746 | C21H23N7S |
| 218.1343 | C20H20N2OS2 | 421.2046 | C14H31N9O2S2 |
| 221.0729 | C8H15NO4S | 422.2133 | C23H34O5S |

What is claimed is:

1. A method of evaluating treatment efficacy in a subject undergoing treatment for tuberculosis comprising the steps of:
   administering a regimen of anti-mycobacterial treatment to the subject undergoing treatment for tuberculosis;
   providing at least two samples from the subject undergoing treatment, wherein the first sample is taken at or before the beginning of the treatment regimen and the second sample is taken at a later time following the initiation of treatment;

measuring the change between the at least two samples in a metabolomic marker selected from the group consisting of Hydroxyproline, N-Acetyl-L-aspartic acid, Dimethyl-L-arginine, N-Acetylasparagine, 1-Methylhistidine, L-Phenylalanine, 2,2,5,5-Tetramethyl-3-pyrrolidinecarboxamide, Pyroglutamic acid, Acetylcysteine, Trigonelline, S-Adenosylhomocysteine, L-Tyrosine, alpha-Aminoadipic acid, Quinolinic acid, Hypoxanthine, and Pyrroline hydroxycarboxylic acid; and correlating the measured change in the marker with a predetermined treatment efficacy.

2. The method according to claim 1 further comprising the step of adjusting the treatment regimen responsive to the correlated treatment efficacy.

3. The method according to claim 1 wherein the subject is treated with a drug selected from the group consisting of isoniazid, rifampin, rifalazil, ethambutol, pyrazinamide, amikacin, moxifloxacin, ciprofloxacin, ofloxacin, kanamycinm, levofloxacin, aminosalicyclic acid, rifapentine, cycloserine, ethionamide, capreomycin, gatifloxacin, viomycin, envyomicin and combinations thereof.

4. The method according to claim 1 wherein the subject is being treated for tuberculosis from a *Mycobacterium* species selected from the group consisting of *Mycobacterium tuberculosis, Mycobacterium bovis, Mycobacterium africanum*, and *Mycobacterium canetti*.

5. The method according to claim 1 wherein the samples are screened in the measuring step by a technique selected from the group consisting of gas chromatography-mass spectrometry and liquid chromatography-mass spectrometry.

6. The method according to claim 1 where the second sample is taken at a timepoint selected from the group consisting of about one week following the initiation of treatment, about two weeks following the initiation of treatment, about four weeks following the initiation of treatment, about six weeks following the initiation of treatment, about two months following the initiation of treatment, about three months following the initiation of treatment, about four months following the initiation of treatment, about five months following the initiation of treatment, about six months following the initiation of treatment, about seven months following the initiation of treatment, about eight months following the initiation of treatment, about nine months following the initiation of treatment, about twelve months following the initiation of treatment, about eighteen months following the initiation of treatment, about twenty-four months following the initiation of treatment, and combinations thereof.

7. The method according to claim 1 wherein the anti-mycobacterial treatment is a drug selected from the group consisting of INH, rifampin, and rifalazil.

8. The method according to claim 1 wherein the sample is selected from the group consisting of urine, sputum, plasma, and serum.

9. A method of evaluating treatment efficacy in a subject undergoing treatment for tuberculosis comprising the steps of:

administering a regimen of anti-mycobacterial treatment to the subject undergoing treatment for tuberculosis;

providing at least two samples from the subject undergoing treatment, wherein the first sample is taken at or before the beginning of the treatment regimen and the second sample is taken at a later time following the initiation of treatment;

measuring the change between the at least two samples in a metabolomic marker having a mass selected from the group consisting of about 109.002, about 147.053, about 166.048, about 183.162, about 206.025, about 267.256, about 277.241, about 279.615, about 280.044, about 281.273, about 295.252, about 357.973, about 388.104, about 406.068, about 410.750, about 428.080, about 444.112, about 463.306, about 499.003, about 504.277, about 534.248, about 545.299, about 557.290, about 609.303, about 654.372, about 696.519, about 742.426, about 799.573, about 805.239, about 817.583, about 850.392, about 859.657, and about 866.366; and correlating the measured change in the marker with a predetermined treatment efficacy.

10. The method according to claim 9 further comprising the step of adjusting the treatment regimen responsive to the correlated treatment efficacy.

11. The method according to claim 9 wherein the subject is treated with a drug selected from the group consisting of isoniazid, rifampin, rifalazil, ethambutol, pyrazinamide, amikacin, moxifloxacin, ciprofloxacin, ofloxacin, kanamycinm, levofloxacin, aminosalicyclic acid, rifapentine, cycloserine, ethionamide, capreomycin, gatifloxacin, viomycin, envyomicin and combinations thereof.

12. The method according to claim 9 wherein the subject is being treated for tuberculosis from a species selected from the group consisting of *Mycobacterium tuberculosis, Mycobacterium bovis, Mycobacterium africanum*, and *Mycobacterium canetti*.

13. The method according to claim 9 wherein the samples are screened in the measuring step by a technique selected from the group consisting of gas chromatography-mass spectrometry and liquid chromatography-mass spectrometry.

14. The method according to claim 9 where the second sample is taken at a timepoint selected from the group consisting of about one week following the initiation of treatment, about two weeks following the initiation of treatment, about four weeks following the initiation of treatment, about six weeks following the initiation of treatment, about two months following the initiation of treatment, about three months following the initiation of treatment, about four months following the initiation of treatment, about five months following the initiation of treatment, about six months following the initiation of treatment, about seven months following the initiation of treatment, about eight months following the initiation of treatment, about nine months following the initiation of treatment, about twelve months following the initiation of treatment, about eighteen months following the initiation of treatment, about twenty-four months following the initiation of treatment, and combinations thereof.

15. The method according to claim 9 wherein the sample is selected from the group consisting of urine, sputum, plasma, and serum.

* * * * *